(12) United States Patent
Lewis et al.

(10) Patent No.: US 7,232,071 B2
(45) Date of Patent: Jun. 19, 2007

(54) SCANNED BEAM IMAGER

(75) Inventors: John R. Lewis, Bellevue, WA (US);
Mark A. Holton, Everett, WA (US);
Martin A. Kykta, Palomar, TX (US);
Frank B. Metting, III, Bothell, WA (US); Christopher A. Wiklof, Everett, WA (US); Christian S. Reyerson, Tucson, AZ (US); Jianhua Xu, Bothell, WA (US)

(73) Assignee: Microvision, Inc., Redmond, WA (US)

( * ) Notice: Subject to any disclaimer, the term of this patent is extended or adjusted under 35 U.S.C. 154(b) by 72 days.

(21) Appl. No.: 10/989,132

(22) Filed: Nov. 15, 2004

(65) Prior Publication Data

US 2005/0116038 A1  Jun. 2, 2005

Related U.S. Application Data

(60) Provisional application No. 60/520,251, filed on Nov. 14, 2003.

(51) Int. Cl.
*G06K 7/10* (2006.01)
(52) U.S. Cl. .............................. 235/462.1; 235/462.39
(58) Field of Classification Search ............ 235/462.1, 235/462.11, 462.13, 462.41, 462.12, 462.39
See application file for complete search history.

(56) References Cited

U.S. PATENT DOCUMENTS 6,590,852 B1 * 7/2003 McCormick, Jr. ...... 369/112.23

* cited by examiner

*Primary Examiner*—Karl D. Frech
(74) *Attorney, Agent, or Firm*—Graybeal Jackson Haley LLP

(57) ABSTRACT

A scanned beam image capture apparatus is adaptable to use in medical imaging applications.

20 Claims, 11 Drawing Sheets

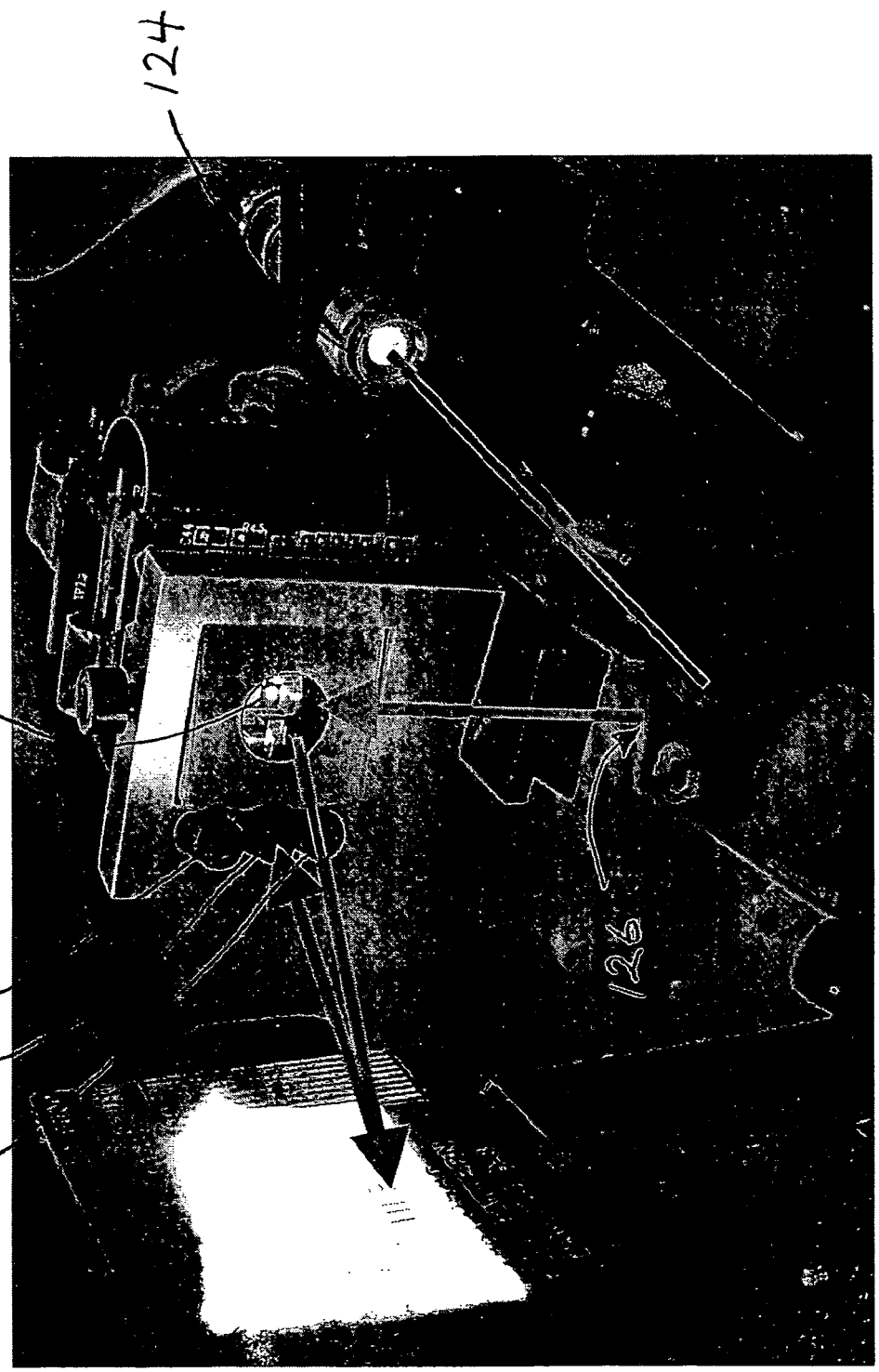

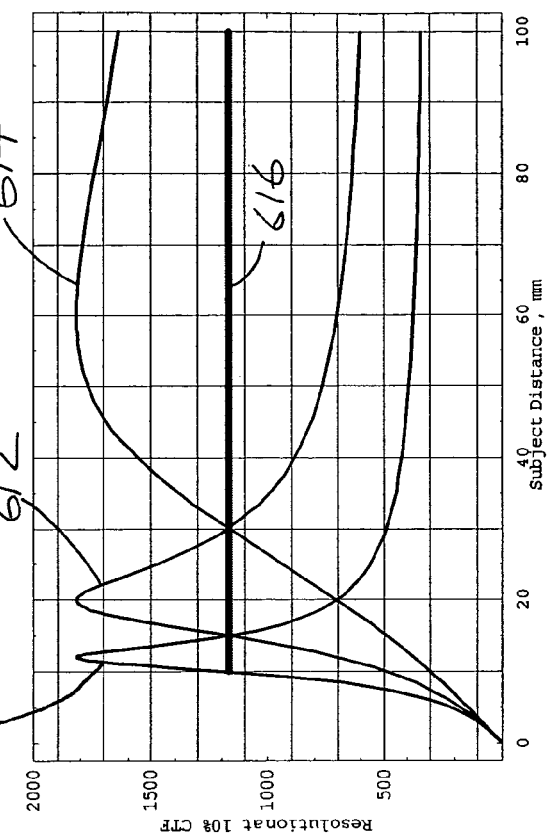
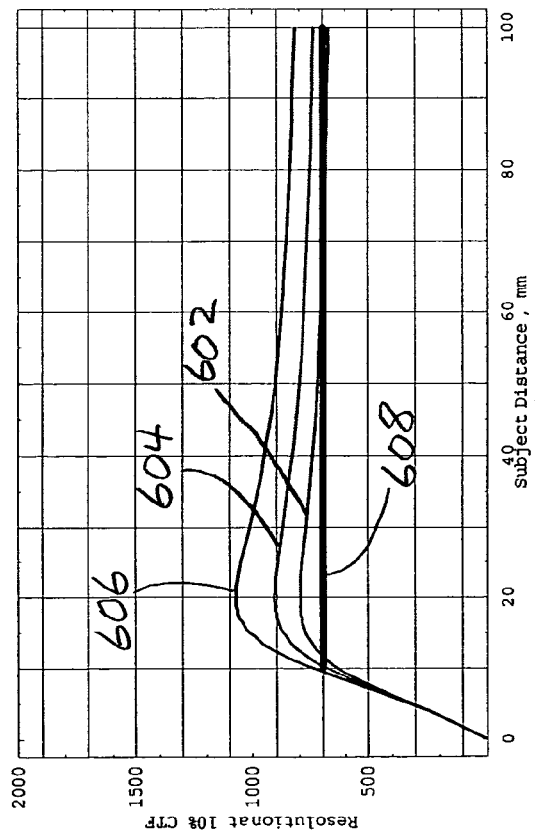

SCANNED BEAM IMAGER

CROSS-REFERENCE

This application claims benefit from and incorporates by reference the copending U.S. Provisional Patent Application Ser. No. 60/520,251, entitled SCANNED BEAM IMAGER, filed Nov. 14, 2003, invented by Lewis, et al., and also claims benefit from and incorporates by reference U.S. patent application Ser. No. 10/873,540, entitled SCANNING ENDOSCOPE, filed Jun. 21, 2004, invented by Wiklof, et al., commonly assigned herewith.

TECHNICAL FIELD

The present invention relates to scanned beam systems, and more particularly to optical imaging systems using scanned beam imaging

BACKGROUND

Endoscopes, boroscopes, laparoscopes, and related visualization devices are used to visualize locations that may not be directly visible to the human eye. One method to relay an image uses coherent fiber bundles. These are flexible and can be long enough to allow the image chip to be part of an external base unit. Unfortunately, coherent fiber bundles frequently suffer from a coarse, often random pixel structure, and hence are viewed as a compromise between image quality and a small diameter flexible form. Another image relay approach is to use discrete lens elements in a short rigid cylindrical form. Over short relays, quite good image quality can be relayed. However, longer relays or smaller diameter leads to compromises. These problems have led to the appearance of video imagers.

Video medical imaging systems such as video endoscopes and video laparoscopes have been in general use since the 1980s. Laparoscopes are rigid devices that may be used in minimally invasive surgery. Typically, laparoscopes use a proximal, externally mounted hand piece that includes a digital camera. The digital camera collects video images through a series of rod lenses arrayed end-to-end inside a tube that extends into a body cavity of the patient. The camera returns its signal through wires to a console that often includes a display monitor. Also typically mounted on the console is a light source, often based on a xenon lamp. The light source sends light to the hand piece through an optical fiber, where a coupling is made. The light is then sent into the body cavity through optical fibers that run inside the laparoscope tube. Often, the optical fibers terminate at the distal end of the tube in a concentric ring, or partial arc around the periphery of the tube. In use, the illumination power is adjusted to give an image of appropriate brightness on the video monitor.

Endoscopes are typically flexible devices that may be used in diagnostic or other procedures. Modern endoscopes (and some laparoscopes) use a distal tip digital camera that collects light, converts it to an electronic signal, and sends the electronic signal up the flexible tube to a hand piece. The signal is then sent to a console for display similar to the manner of operation of laparoscopes. Illumination is sent to the body cavity in a manner similar to that of laparoscopes, except the illumination fibers typically terminate as a pair of apertures on each side of the camera lens. Endoscopes often include irrigation channels and working channels for instruments, in addition to a steering apparatus that may be used to aim the tip of the endoscope in the direction the clinician wishes to look or push the tube.

Endoscopes and laparoscopes may be end-looking or side-looking. In end-looking devices, the field-of-view is positioned directly in front of the end of the device. Side-looking devices may have their fields-of-view located 70°, or other angle off-axis from the end of the tube. The field-of-view varies according to the application. For instance, colonoscopes (a type of endoscope used to examine the colon) often have a 140° diagonal field-of-view, while laparoscopes may have fields-of-view closer to 70° diagonal.

Instruments may be passed down the working channel of many endoscopes. Forceps and other devices have been developed that may pass within the diameter of the working channel into the body cavity where the clinician uses them to take tissue samples, etc. In the field of laparoscopy, instruments are generally introduced to the procedure through separate small incisions. Often the instruments as well as the laparoscope pass through trocars, or rings that line the incisions to prevent undue binding or damage as well as maintain a seal.

Laparoscopes and endoscopes may use a pixelated sensor array such as a charge-coupled device (CCD) or complementary metal oxide semiconductor (CMOS) device. In pixelated imagers, each pixel corresponds to an element of an array and each element receives light energy from a conjugate point in the field-of-view for a selected sampling interval. Each element converts light to an electrical signal proportional to the brightness of its conjugate point. This approach may force compromises in meeting the size and image quality requirements. In many cases, achieving the highest performance with such technologies implies imaging chips that are large. Some large chips depend on an optical system to relay the image from the interior of the body to the camera chip. In many cases, such sysetems also depend on strong illumination, typically derived from a 300-watt arc lamp coupled in by fiber bundle.

One announced video endoscope product has a pixel count of 850,000 and fits in a probe with tip diameter of 5.9 mm. To increase the number of pixels or decrease the probe diameter, one approach is to reduce the pixel size on the imaging chip. Smaller pixels (below 4 microns) frequently run into difficulties with electron diffusion, and hence scaling down may compromise resolution, such as by limiting sampled point density, for example, contrast ratio, and/or other aspects of the image. Pixel array technology may also suffer from the limitation of fixed pattern noise. This may have the form of both offset fixed pattern (which may dominate in low level regions) and gain fixed pattern (which may affect even high signal areas of the scene). Typical non-uniformity may approximate or exceed 1% of the average signal level. Thus with CCD and CMOS technologies it is frequently considered challenging to increasing the sampling density while also reducing instrument size.

Color distal video chip systems present further challenges. One choice is to use a single chip sensor and divide the sample points spatially by a factor of 3 (or by 4 in red and blue channels and by 2 in the green channel), with red, green, and blue color filters over individual pixels. This typically causes a loss of ⅔ of the light at the sensor plane. Conversely, a three-chip sensor, such as is used in high-quality cameras, is frequently bulky compared to a single chip and is incompatible with size constraints. Time sequential color is another approach, but this allows only ⅓ of the time for photon collection, or alternatively ⅓ the video rate.

Another challenge is in crating a driver for a high bit rate data link that must somehow be contained in the small volume of the distal tip.

Thus, today's digital endoscopes and laparoscopes may suffer from limited image quality and dynamic range and often exhibit other undesirable artifacts. In the case of distal imaging systems in particular, diameter limitations have been a common hindrance to higher resolution. Conversely, resolution requirements have hindered diameter reductions.

Overview

According to one aspect, a scanned beam imaging device, which may be fabricated in the form of an endoscope for example, has advantages over present CCD imaging technology. Advantages can include some or all of an increase in image resolution, an increase in image quality, a reduction of light source power, and a reduction in package diameter.

According to another aspect, a scanned beam endoscope has a diameter of 5 millimeters.

According to another aspect, a scanned beam endoscope has a scanner capsule with a diameter of 2.5 millimeters (mm).

According to another aspect, a scanned beam imaging system may include a photonics module with red, green, and blue laser light sources at 635 nanometers (nm), 532 nm, and 473 nm wavelength, respectively.

According to another aspect the photonics module may combine light from the laser light sources using dichroic mirrors and launch the combined light into a single mode optical fiber.

According to another aspect, the combined light is transported down the single mode optical fiber to a distal location, which may be in a non-readily accessible location such as inside a body.

According to another aspect, light emerging from the distal end of the single mode optical fiber is formed into a beam and reflected off a first reflecting surface onto a bi-axial MEMS scanner. The bi-axial MEMS scanner then scans the beam over a two-dimensional field of view.

In one particular embodiment, the MEMS scanner had a 1.56 mm square mirror and scanned the beam at a horizontal (fast) scan angle of 6 degrees zero to peak mechanical at a (fast scan) frequency of 19.7 kilohertz (kHz). The vertical scan approximated a sawtooth waveform and progressively scanned the beam at a slow scan frame rate of 60 hertz (Hz).

According to other embodiments, the horizontal and vertical scans may be run at frequencies of several times the frame rate to produce a Lissajous scan pattern from which an image may be decoded.

According to one embodiment, the light from the distal end of the fiber passes through a hole in the MEMS scanner. The first reflecting surface is the inside of a meniscus lens that reflects a portion of the light, the rest of the light propagating through to the field-of-view as a non-scanned pattern. The reflected portion of the light is reflected to the MEMS scanner and scanned across at least a portion of the meniscus lens as a diverging beam. Scanned light that passes through the meniscus lens is focused to form a scanned beam with a desired shape, for example a semi-collimated beam having a waist of desired size at a desired distance. The shaped scanned beam thus sequentially illuminates spots on the target object.

According to one embodiment, the scanned beam had a power of 1 to 3 milliwatts (mw) that impinged the test object at a distance of 10 to 100 mm.

According to one embodiment, scattered light from the scanned beam was collected by several 3 mm diameter multimode fibers. The collected light propagated along the multimode fibers a distance of approximately 1 meter where it was converted to electrical signals by detectors.

According to one embodiment, the detected light was digitized and reconstructed to form an image of the test object with a resolution of 800 by 600 output pixels.

According to another embodiment, a scanned beam imaging device includes separable controller and tip sections.

According to another embodiment a controller can support a variety of tips.

BRIEF DESCRIPTION OF THE FIGURES

FIG. 2A is a perspective view of a bench-top prototype scanned beam imager.

FIG. 6A shows resolution for red, green, and blue for an unclipped Gaussian beam with half width at $1/e^2$ intensity of 55 microns.

FIG. 6B shows resolution as a function of distance for green at three different focal settings for an unclipped Gaussian beam of 110 microns half width at $1/e^2$ intensity.

DETAILED DESCRIPTION

Scanned beam imaging offers a good solution to many requirements, even given the constraint of small diameter and remote operation. The technology is simple and optically transparent, allowing the possibility of limited use or even disposable endoscopes; and allowing imaging modalities such as fluorescence imaging, or multi-spectral imaging for example. According to one embodiment, the light detector is in the base unit, and hence allowing for very high quality without burdening the tip with high cost.

In comparison to a matrix sensor, the optics for a scanned beam imager may be simpler and achieve higher performance with less expense. The reason for this is that the scan mirror takes a single on-axis well-formed point spread function (PSF), and scans it over the field using reflection from a flat mirror. In comparison, a matrix image a good PSF must be formed over the entire array of a million or so pixels. This can be a much more difficult optical design problem.

Figure 1:
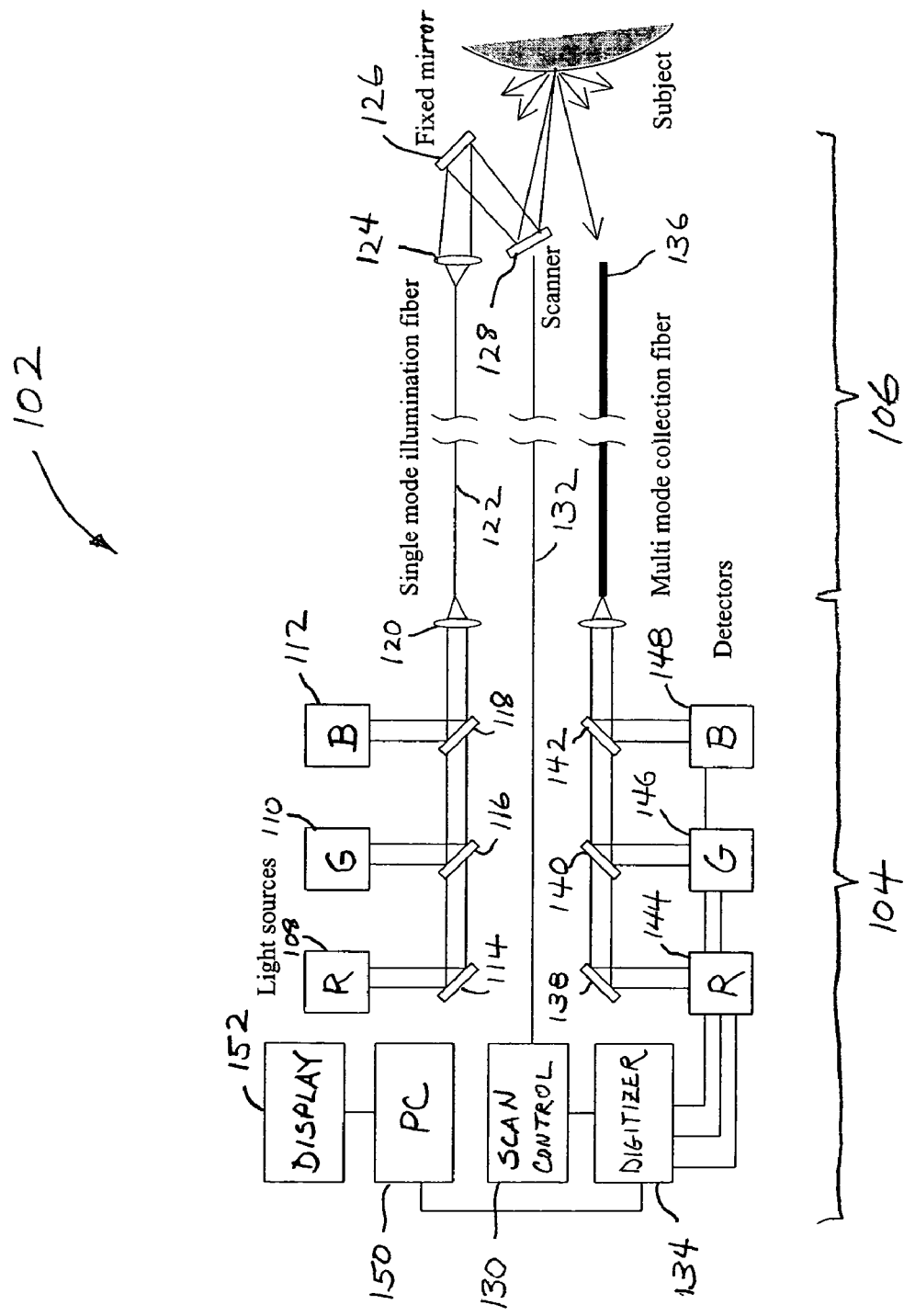
FIG. 1 is a block diagram of a scanned beam imaging system, showing signal path from light sources to scanner, object, detectors and computer.

FIG. 1 a block diagram of a scanned beam imaging system 102, showing signal path from light sources to scanner, object, detectors and computer. Scanned beam imaging system 102 may be formed as two sections—a proximal or controller section 104, and a distal or tip section 106. According to one embodiment, the tip 106 may be detached from the controller 104. Such a detachable tip may be cleaned for reuse, or alternatively may be made disposable with a new tip being attached for subsequent procedures.

Lasers 108, 110, and 112 at the wavelengths and power noted in Table 1 are combined using dichroic mirrors 114, 116, and 118 and launched by coupling 120 into a single mode (illuminating) fiber 122. According to one embodiment, the illuminating fiber 122 had a length of 3 meters. The combined beam emerges from the distal end of illuminating fiber 122, is formed into a beam by beam-shaping optics 124, and is reflected from a fixed mirror 126 onto the MEMS scanner 128.

The MEMS scanner 128 was driven by scan control electronics 130 through electrical conductors 132. Electrical conductors 132 also supply a scanner synchronization signal to the digitizer 134.

The scanning mirror directs the beam across a field of view. Light reflected from objects in the field of view is collected by multimode fibers 136 and propagated a distance of about 1.5 meters to the controller 104. Dichroic mirrors 138, 140, and 142 separate the reflected light into wavelength respective wavelength components for detection by red, green, and blue detectors 144, 146, and 148.

In an alternative embodiment, a separate multimode fiber may be dedicated to each detector. The image of FIG. 3 was created using this alternative embodiment. One side effect of using separate collection fibers is the appearance of color shadows or glare spots, depending upon the relative positions of the fiber distal end locations. This approach may be used to provide additional information about the object.

Returning for the moment to FIG. 1, electrical signals from detectors 144, 146, and 148 are digitized by digitizer 134, making use of a synchronization signal from the scan drive. The detected light signals are then processed by processor 150, which for one embodiment was a personal computer, and stored and/or displayed on display 152. To provide compatibility with legacy NTSC equipment, a graphics card with NTSC output as well as digital video was used.

FIG. 2A illustrates a laboratory embodiment showing beam shaping optics 124, fixed mirror 126, and beam scanner 128. The collection ends of three collection fibers 136a, 136b, and 136c may also be seen.

Figure 2B:
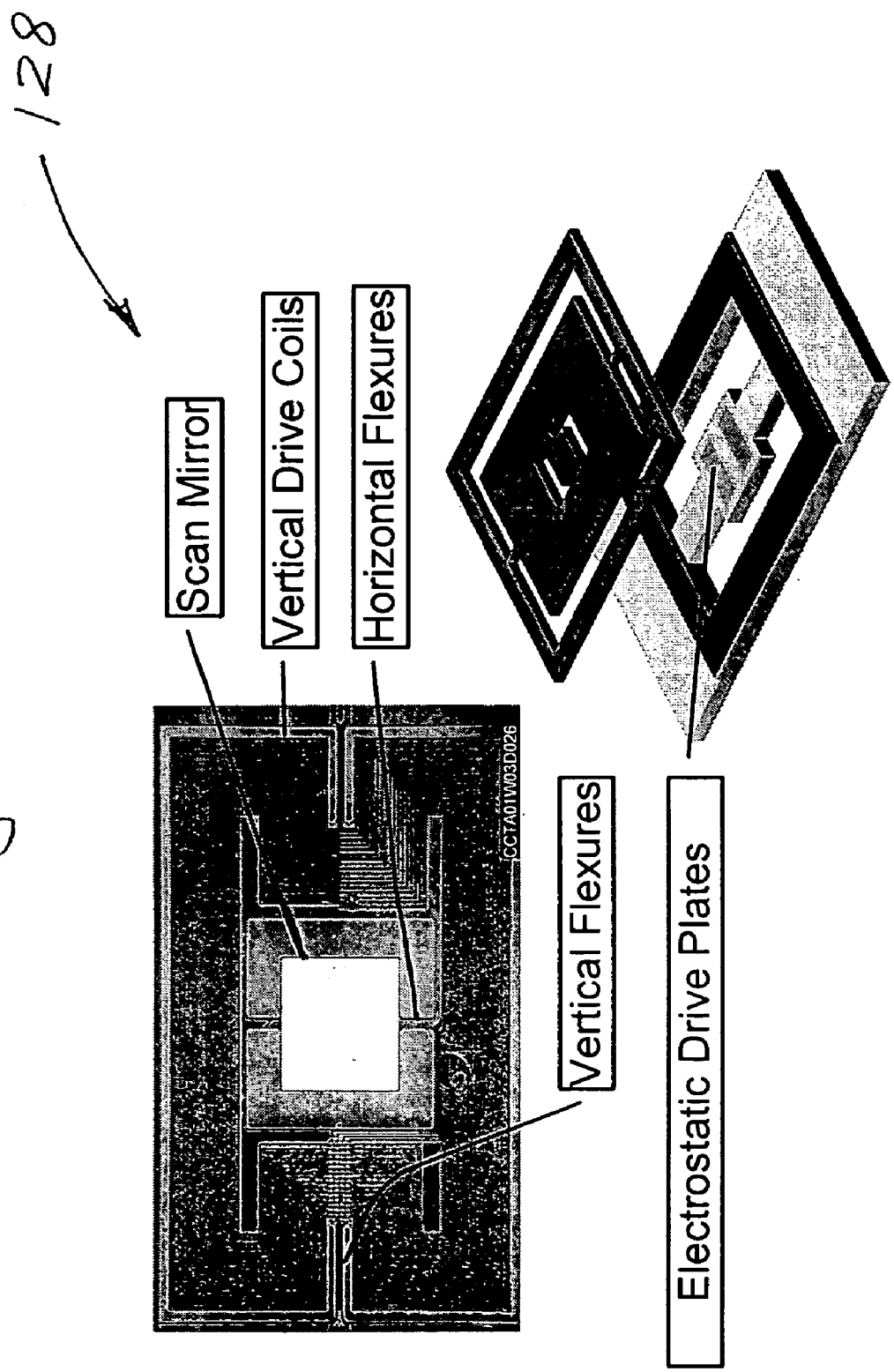
FIG. 2B is a diagram showing a MEMS scanner used by the system of FIG. 2A to scan the light beam. The housing and magnets for the slow scan drive are omitted for clarity.

FIG. 2B illustrates the construction of MEMS scanner 128 used in the laboratory embodiment of FIG. 2A. The scanner chip has scan mirror 1.56 mm square and the overall dimension of 7 by 13 mm. The mirror is attached via torsion flexures that resonate at 19,700 Hz. This mirror is driven electrostatically to an amplitude of about 6 degrees zero to peak mechanical angle. This results in a total optical scan angle of 24 degrees. The fast scan mirror is carried on a gimbal structure that is in turn attached to a frame by flexures that have about a 600 Hz Resonance. This gimbal is driven by magnetic forces on conductors placed on it. The coils have sufficient torque so that a control circuit can provide a high quality linear ramp motion with a rapid retrace. The control circuit and algorithm provide better than 1% speed uniformity, and 88% scan availability.

Both axes of MEMS scanner 128 have angle feedback via piezoelectric resistance (PZR) strain gauges built into the flexures. These signals are part of a DAC—DSP—ADC loop that finds and maintains the resonance of the fast scan, controls the slow scan, and provides horizontal and vertical synchronization timing signals for interface with the digitizer 134.

The scanner 128 of FIGS. 2A and 2B is packaged in vacuum to reduce gas viscous friction and allow the small electrostatic forces provided by plate drive to build up to the 6 degree oscillation. The stability of this scanner and control system has been proven to have sub-pixel positional precision. The optical properties of the scanner 128 of FIGS. 2A and 2B have been measured by stroboscopic interferogram and numerous other measurements to be optically flat to the degree needed for the application.

Figure 3:
FIG. 3 is an image of a USAF 1951 resolution target captured by the system of FIG. 2A at a working distance of 50 millimeters.

The power and signal levels for the image shown in FIG. 3 are listed in Table 1. For the laboratory apparatus, little attempt was made to optimize the coupling of laser power to the scanned beam, it being only necessary to get enough light in the scanned beam to provide acceptable signal-to-noise ratio. The three multimode light collecting fibers 136a, 136b, and 136c each had a 3 mm diameter core, a numerical aperture (NA) of 0.63, and a transmittance of greater than 85% across the visible spectrum. Because of the 1:1 correspondence of collection fibers to detectors, dichroic mirrors 138, 140, and 142 were not used. The detectors 144, 146, and 148 were avalanche photodiodes with 5 mm diameter active area and estimated quantum efficiency (QE) of greater than 80% across the visible spectrum. Due to the avalanche gain of these devices, the limiting noise is due to photon statistics. Using the energy of the photon for each wavelength, the table shows the number of photons arriving in a 20 nanosecond sample period. Poisson statistics gives the signal-to-noise ratio as reciprocal square root of this number, as shown in the last column.

TABLE 1

Wavelengths, power and signal levels.

| Channel | Laser Wavelength [nm] | Laser Power [mW] | Scanned Beam Power [mW] | 3 mm dia. Collected power at 100 mm range [µW] | Collected photons at 100 mm range and 20 nsec | Shot Noise SNR at 80% QE and 30% reflectance |
|---|---|---|---|---|---|---|
| Red | 635 | 30 | 2.7 | .60 | 38,000 | 96 |
| Green | 532 | 15 | 3.3 | .74 | 39,000 | 97 |
| Blue | 473 | 10 | 1.0 | .22 | 10,000 | 50 |

The signals from the detectors 144, 146, and 148 were digitized at 50 M samples per second. A complete frame was captured in ⅟60 second. Single images could be saved to disk, and then be reconstructed using interpolation algorithms. Other software with simplified transformations gave a real time preview of 10 frames per second. This limit was not due to the scanner but rather the transfer rate of the digitizer card used for the laboratory embodiment.

An image, captured by the system and shown in FIG. 3, is of a standard test target—USAF 1951. Close inspection (circled) of this target shows resolution down to group 3 element 4. This corresponds to a resolution of 11.3 line pairs per mm. The distance to the object in these tests was 50 mm. resulting in an approximately 20 mm horizontal field of view. This implies 510 lines (205 line pairs) across the image. The image compared well in side by side viewing with a 10 mm diameter rigid endoscope having a proximal 3-chip camera.

By using MEMS, and, at least in some embodiments, passive fiber optics for the probe tip 106, the cost of the probe tip may be kept to a minimum. Probe tips of differing scan angle, size of collection fiber, scan frequency, and/or focal characteristics may be supported by a base unit. In addition, the number of wavelengths launched, and the number of wavelengths collected may be changed. According to some embodiments, this may be a property of the base unit 104 independent of the probe used. The following sections show how this is done for a wide field-of-view flexible endoscope probe with a 5 mm overall diameter.

Figure 4A:
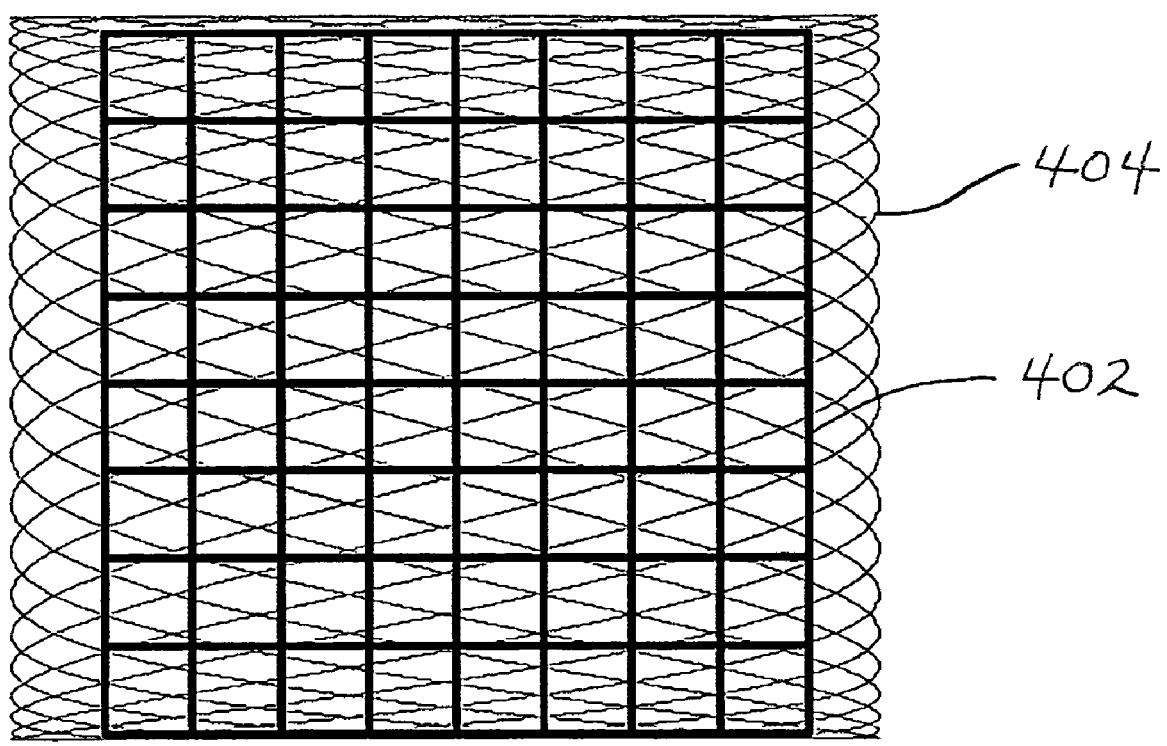
FIG. 4A is a diagram comparing a bi-sinusoidal scan trajectory to a rectilinear pixel grid.

To reduce power requirements and size constraints at the imaging tip, some embodiments may allow both scan axes to scan resonantly. A resultant idealized bi-resonant or bi-sinusoidal scan pattern is shown in FIG. 4A. In certain instances, the scan pattern follows a path characterized as a Lissajous pattern. Rectilinear matrix 402 is shown overlaid with bi-resonant scan path 404. In this case, the intersections between the vertical and horizontal lines of the rectilinear matrix represent idealized pixel positions while bi-resonant scan path 404 represents the actual path taken by the scanned spot. As may be seen, the actual scan path doesn't align perfectly with all the rectilinear pixel positions. These values may therefore be determined by interpolating.

Methods for selecting bi-resonant frequencies as well as methods for maximizing the image quality are discussed analogously in the U.S. Patent Application entitled IMAGE QUALITY CONSIDERATIONS IN BI-SINUSOIDALLY SCANNED RETINAL SCANNING DISPLAY SYSTEMS, by Margaret Brown, Marc Freeman, and John R. Lewis, U.S. application Ser. No. 10/441,916, applied for May 19, 2003, commonly assigned herewith and hereby incorporated by reference. That patent application, among other things, teaches methods of interpolating pixel values, particularly with respect to bi-sinusoidal scanning.

Figure 4C:
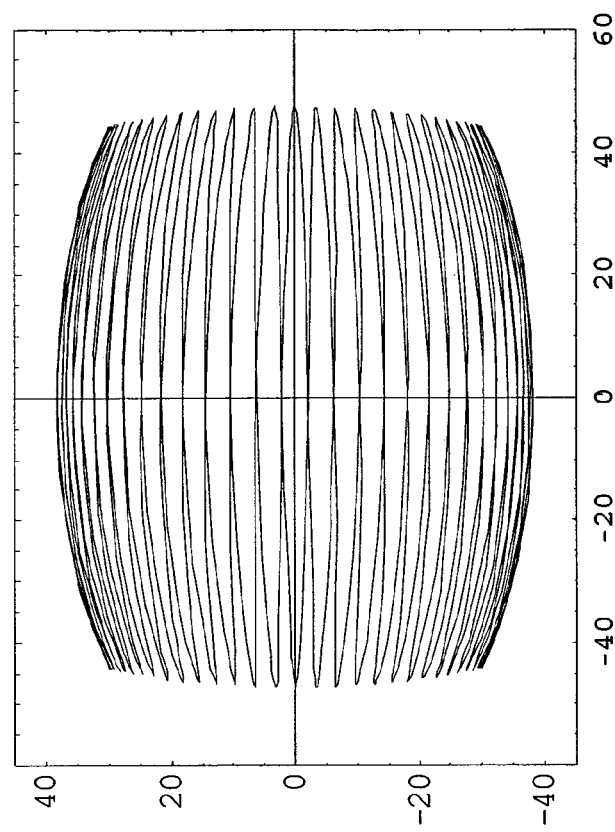
FIG. 4C shows one mapping of the scan trajectory of FIG. 4A onto a plane.
Figure 4B:
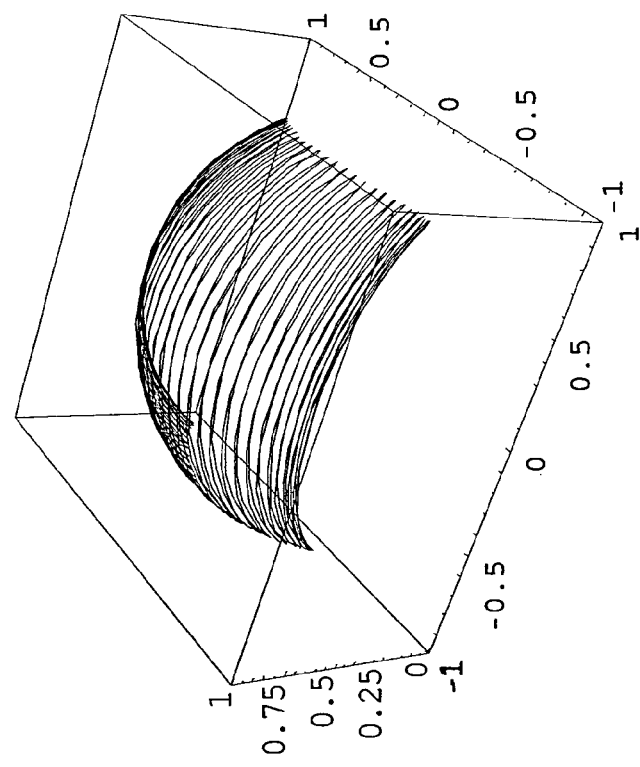
FIG. 4B is a scan trajectory in spherical coordinates.

At large scan angles, the concept of a two-dimensional scan begins to run in to effects of solid geometry. This can be accounted for in reconstruction by choice of mapping function. This is illustrated in three dimensions in FIG. 4B, for a case where the mechanical rotation amplitude is 28 degrees zero to peak for the inner flexure, and 21 degrees for the outer flexure. Because of inertia considerations the inner flexure is chosen for the higher frequency resonance. This design form is used to pick amplitudes and frequencies that match the application. The amplitudes are chosen to cover the field of view specified by the application. Various approaches can be taken in mapping the 3 dimensional scan pattern to the two dimensional display. One approach is to present all the data collected by using a mapping function that uses the flexure angles to map to the display buffer indexes. Another approach is to use the polar angle and a radial function to map onto the plane. This has the advantage of keeping scan geometry constant as the probe may be rotated about its axis. One such mapping is shown in FIG. 4C.

Once the amplitudes have been set, then scan frequencies are chosen to meet sample density requirements for the given point spread function size. Along the scan direction, sample density is set by the electronic sample rate, and hence can be as high as necessary without impacting scanner design. Transverse to the scan, there will be finite gaps between lines. These lines must be spaced closely enough so as to match the sampling requirements. The spacing is dictated by the fast scan frequency, the frame time and vertical field. In contrast to fixed array devices like a CCD, this sample density can be increased 10 fold by allowing a ⅙ second exposure time such as in a documentation study. The scan density can be much thinner for ⅟60 second real time motion interaction where detail is not being studied.

Coding and information theory, and bandwidth conservation concepts can now be applied. For example in streaming video, all pixels are typically linear combination of compressed data (for example DCT is used in mpeg). Thus image data becomes a series of coefficients, rather than a table of pixel values. Output values are formed from functions and linear combinations of the sample values. This allows bidirectional sampling, and compensation for the non-uniform sample densities arising from the sinusoidal motion.

Figure 5B:
FIG. 5B is a simulation of a scanned beam image captured after several vertical cycles of a bi-sinusoidal trajectory.
Figure 5A:
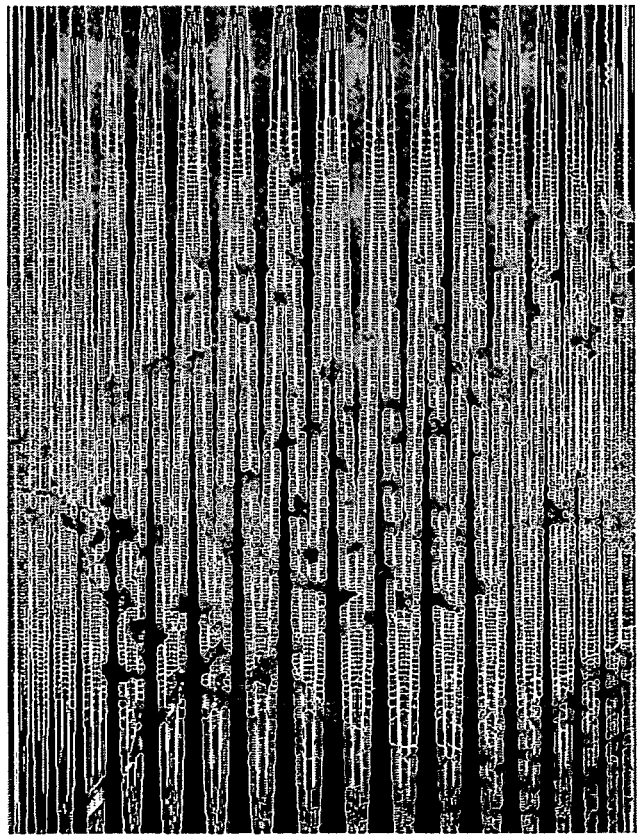
FIG. 5A is a simulation of scanned beam image captured after two vertical cycles of a bi-sinusoidal trajectory.

FIGS. 5A and 5B show how samples from a bi-sinusoidal scan are used to build up a complete image. The bi-axial bi-resonant scanner has frequencies of 23,600 and 575 Hz in this simulation. A generalization of the frame rate is the greatest common divisor (GCD) of these two frequencies—25 Hz. In ⅟25 of a second there are 23 vertical periods and 944 horizontal periods. FIG. 5A shows the results after 3 vertical periods of an interleaved scan have been written to the display plane. FIG. 5B is after 23 periods and still shows gaps that, in this exemplary algorithm, are filled in by interpolation. As samples come in they are distributed to a region near an address derived from the known scan geometry. One sample affects nearby addresses according to a set of weighting coefficients. The weighting coefficients are developed by applying image quality metrics in a simulation environment. This allows one to develop optimal image quality for a given level of scanner performance. It is a quantitative exercise.

Referring again to FIG. 1, the light collected at the distal tip is transmitted, band separated and delivered to detectors with little loss. By the use of avalanche photodiodes (APD) as detectors, large area (5 mm diameter), high quantum efficiency (greater than 80%) and high bandwidth were achieved. As range to objects increases, collected light will decrease, if all else is held constant. Beyond a given range, noise may begin to dominate the signal.

More scanned beam power is one remedy to this. At greater distances, one is justified in increasing scanned beam power so that the average irradiance is the same for the near as well as the far case. The problem with increasing the light source power is that in a scene with near and far objects, the near by objects may be driven over limits. In a scanned beam system, it is possible to control the probing power on a pixel-by-pixel basis or as a function of an exposure mask. One method for controlling probing power is described in U.S. patent application Ser. No. 10/630,062, entitled METHOD AND APPARATUS FOR ILLUMINATING A FIELD-OF-VIEW AND CAPTURING AN IMAGE, invented by Christopher A. Wiklof et al, filed Jul. 29, 2003, commonly assigned herewith and hereby incorporated by reference.

An exposure mask may provide a simplified approach to controlling power. Such a mask may, for example, recognize that for many applications, the center of the field-of-view typically has an object distance much greater than that of the edges of the field of view. In such cases, all other things being equal, one can increase the amount of illuminator power at the center of the field-of-view and decrease it at the edges. Additionally or alternatively, one may compensate for collection fiber efficiency or modify collection fiber efficiency to compensate for the greater amount of light returned by close objects. Thus, an exposure mask may serve to modulate light source power, detected signal digitization, or may be an optical device, such as a gradient filter, that modifies the amount of signal returned to the processor as a function of region within the field-of-view.

Powerful lasers and efficient coupling can supply many times the power used in the laboratory embodiment described above. The amount of power projected may limited by safe irradiance of the object rather than a technological limit. Using these criteria, then an expression for the received signal can be written in terms of the irradiance on the object. The expression is (neglecting cosine factors):

$$P_{collect} = A_{collect} \Omega_{project} \frac{1}{\pi} E_{object} \quad (1)$$

This result is in fundamental terms and has a simple interpretation. If the collector angle is matched to the projection angle (or larger) as it should, then the collected power is the etendu of the collection fiber times the luminance of the object. The large NA (0.63) of a multimode fiber makes it an area efficient light collector especially when compared to a camera lens and Matrix chip. An APD of 5 mm diameter and Lambertian acceptance provides enough etendu to support several such fibers, resulting in a large collected power for a given object irradiance.

One may safely implement this using very high maximum power with interlocks based on sensing returns to ensure that nearby objects are not irradiated at a power level meant for distant objects.

FIGS. 6A and 6B illustrate resolution as functions of distance. The criteria used for resolution was number of lines across the format width that would result in a contrast transfer function (CTF) of 10%. This gives a pixel count which is 1.67 times that which would be given by applying a full width half maximum (FWHM) definition for a pixel, but is more in line with how camera lenses are rated.

FIG. 6A shows a fixed focus design using a 200 micron diameter scan mirror. The three curves on the graph 602, 604, and 606 represent the resolution for the red, green and blue wavelengths, respectively. The heavy line 608 is drawn for 700 pixel resolution at 10% CTF. This graph shows that the expected resolution for all colors is better than 700 pixels over the entire 10 to 100 mm operating range of the instrument without refocusing. This performance is obtained with a beam diameter described by a Gaussian "w" parameter (half width at $1/e^2$ intensity) of 55 microns at the mirror. Clipping at 2w/D of 0.75 and also allowing for an inclination of 35 degrees results in a mirror diameter of 200 microns for this case. Other degradations such as mirror deformation, beam clipping, projection lens aberrations, and amplifier bandwidth are not accounted for here, but are small compared to the beam propagation.

Resolution curves for a high-resolution case using a 400 micron diameter scan mirror are shown in FIG. 6B. This case uses a "w" parameter of 110 microns, which is twice that of the fixed focus case. The larger mirror size gives twice the resolution and four times the number of pixels. The greater resolution comes at a cost of reduced depth of field. The graph of FIG. 6B shows resolved lines vs. distance curves 610, 612, and 614 for three different focal settings corresponding to 12 mm, 20 mm, and 60 mm, respectively. The three focal length settings result in greater than 1170 lines resolution, shown by line 616, is obtained over the entire range of 10 to 100 mm. Alternatively, if continuous focus is implemented, 1700 lines of resolution may be obtained. As indicated above, the resultant mirror diameter requirement (using same rules as for the case illustrated by FIG. 6A) is 400 microns.

A different mirror size, for example of 500 microns, may be used for the scanner to allow for other degradations in the MTF due to bandwidth, mirror deformations and motional blur.

Figure 7B:
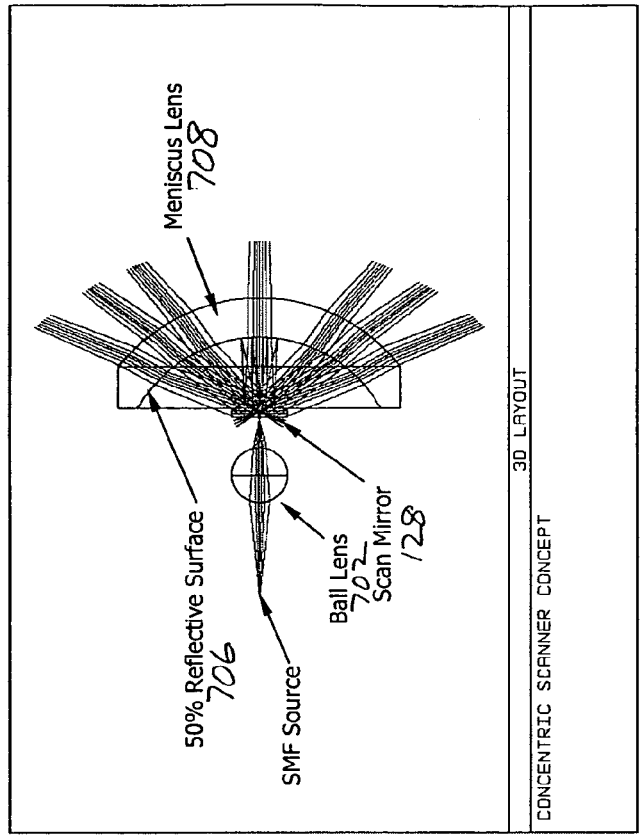
FIG. 7B is a ray trace showing light propagation through the distal tip scan optic of FIG. 7A.
Figure 7A:
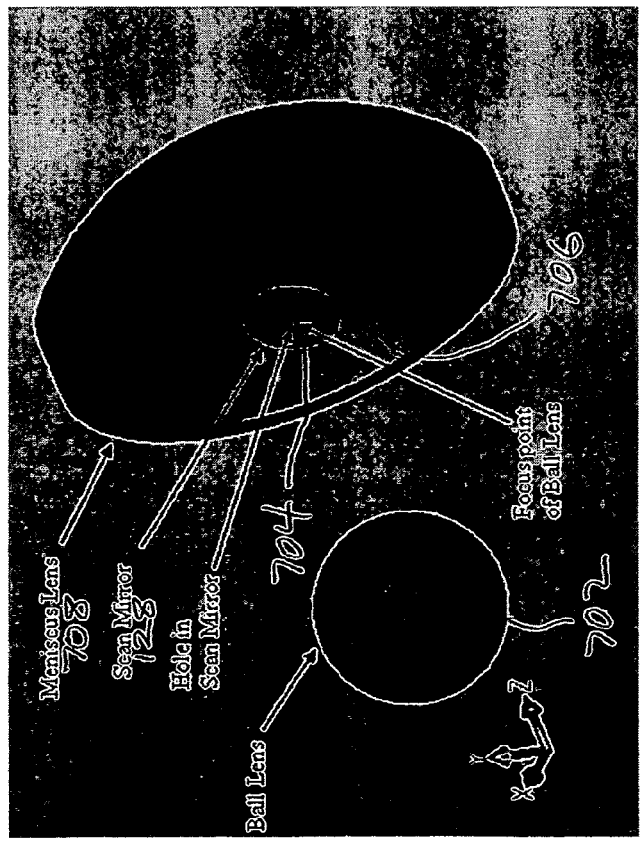
FIG. 7A is a solid view showing the spatial relationships of some essential elements of a distal tip scan optic.
Figure 9:
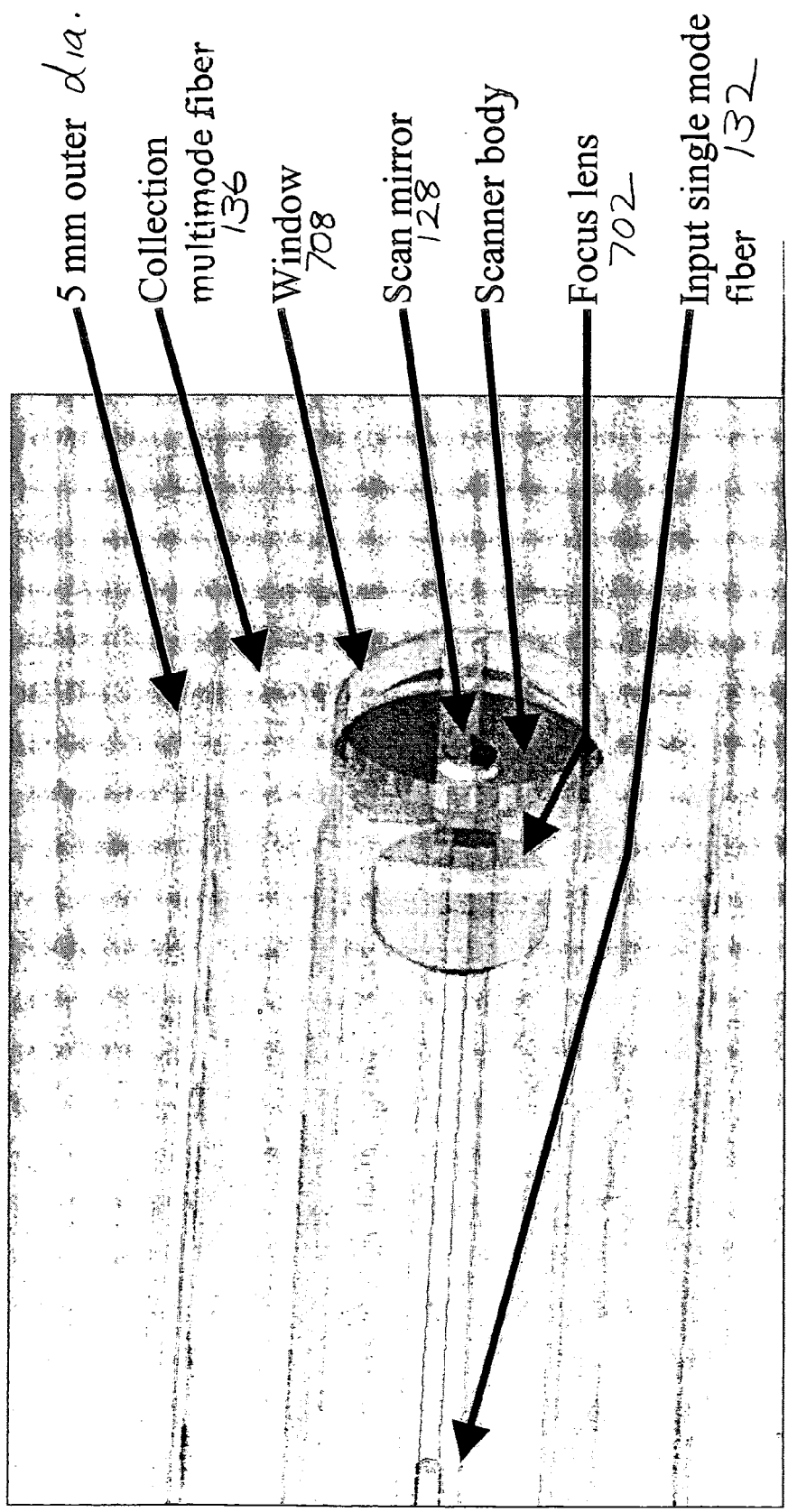
FIG. 9 is a perspective view of an embodiment of the distal tip of a scanned beam endoscope.

FIGS. 7A and 7B illustrate a probe tip optical design compatible with the requirements to achieve resolutions illustrated by FIGS. 6A and 6B within a compact tip geometry using a 2.5 mm diameter capsule and 5 mm overall diameter illustrated by FIG. 9. Laser output from a single mode fiber is focused by a lens 702 (here a ball lens) through a small hole 704 in the center of the scan mirror 128. Using a hole size that is 10% of the mirror diameter costs only 1–2% in power (mirror area), and is quite acceptable. In this case the hole is 50 microns. After passing through the hole, the light then diverges and is then converged and reflected back onto the scanner surface by the concave inner surface 706 of the meniscus lens 708. Surface 706 is coated to be 50% transmissive and 50% reflective. The scan mirror 128 then reflects this light back towards the meniscus lens and now 50% transmits out of the scan cavity forming a Gaussian spot on the tissue surface. Because the closest point is 10 mm, the resulting value for f/D together with little power on the beam after reflection from the scan mirror results in near diffraction limited performance.

This double pass setup allows for a very compact design, albeit at the expense of higher laser power requirements. The safe operating power depends on the external beam and is unchanged by these internal losses. An additional issue with this compact design is that the first pass light is non-scanned, and will offset the scanned beam signal. Signal processing (high pass filtering) is used to reduce this effect.

FIG. 7B illustrates a ray trace for the probe tip design shown in FIG. 7A.

Figure 8B:
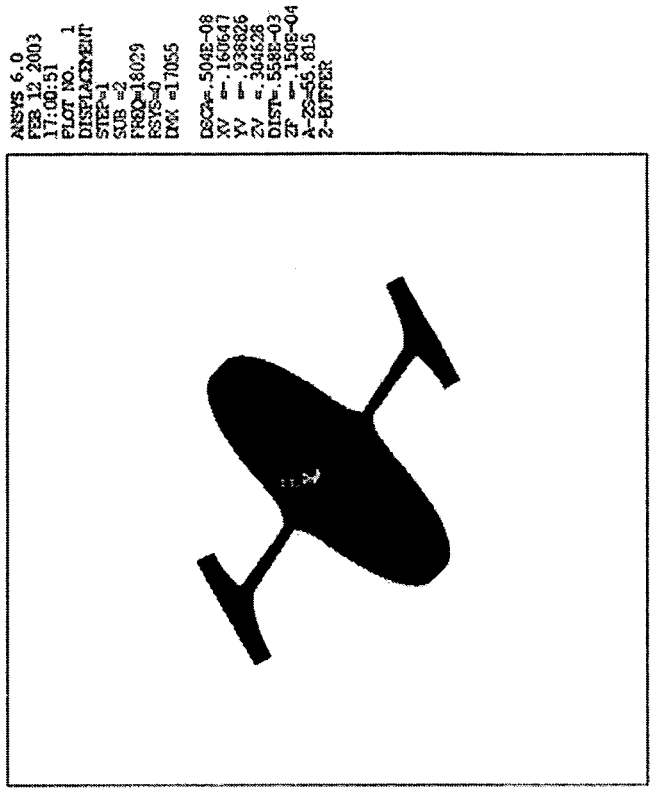
FIG. 8B is a stress analysis for deformations at full scan angle.
Figure 8A:
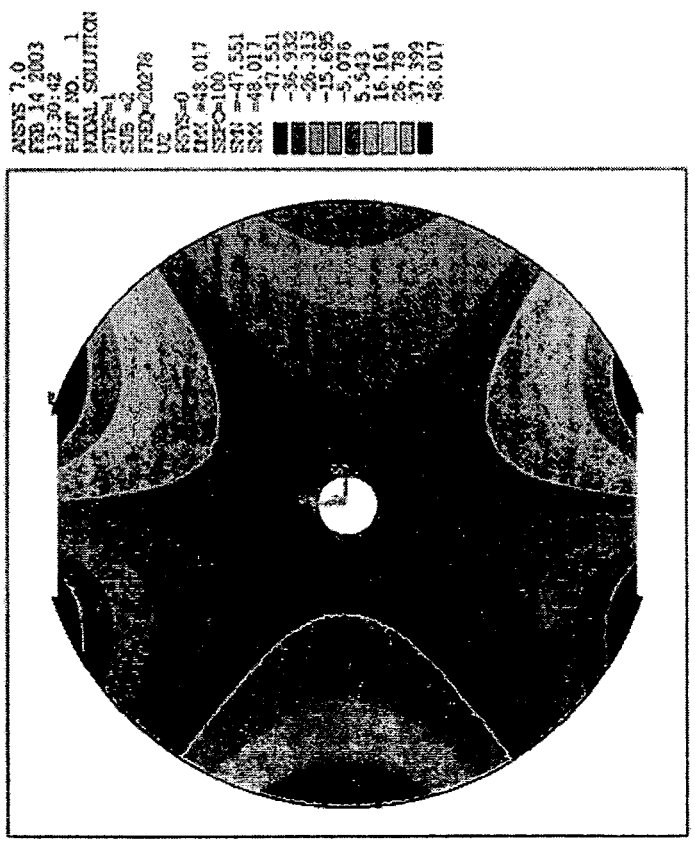
FIG. 8A is a Finite Element Analysis (FEA) result showing mirror distortion due to acceleration stresses.

FIGS. 8A and 8B illustrate MEMS scanner deformation performance. Addressing dynamic flatness, consider a dimensional analysis of the deformation of a scan mirror 128:

$$\frac{\delta_{max}}{\lambda} = k_2 \frac{\rho}{E} \frac{\theta_{MMSA} D}{\lambda} \left(\frac{D}{t_m}\right)^2 f^2 D^2 \quad (2)$$

In this expression $k_2$ is a numeric that depends on the design form, $\rho/E$ is characteristic of the material, and $\theta_{MMSA} D/\lambda$ is proportional via optics to the pixel count on a scan line. The ratio $D/t_m$ is the aspect ratio (diameter to thickness) of the form, which is invariant to scaling. The frequency f is given by refresh rate and sample density requirements.

Keeping these factors constant, one can scale down D to reduce the deformation. The pixel count goal then dictates $\theta_{MMSA}$. This then is limited by optical design. An exemplary embodiment uses 500 microns for D, and depending on process constraints, determined a thickness that would yield acceptable deformations. The results of that process are shown in FIG. 8A. The deformation shape is characteristic of this design form. The addition of a small hole to allow for the beam path did not introduce any noticeable effects. The deformations are approximately +/−50 nanometers peak as determined by finite element analysis. The conclusion is that optical aberrations are within range of acceptability.

Mirror frequency, mirror inertia, and scan angle determine a mirror kinetic energy that is exchanged in resonance with an equal amount of potential energy stored in the flexure as stress. By making the flexure volume large enough, the maximum energy per unit volume and hence the stress limit of the material limit can be met. One question is then how to maintain compactness. In addition to enlarging the part, longer flexures lower the frequency of undesirable modes that must also be checked. The designer uses normal optimization techniques to arrive at a design, the result of which is shown in FIG. 8B. The flexure stress is below the value used as a design value, and the flexure length is consistent with the desired 2.5 mm diameter scanner package.

To actuate the scanner, an appropriate compact means is used. This requires balancing the damping losses against the power generated by the actuator. In practice, electrostatic (e.g. capacitive plate or interdigitated fingers), magnetic, and piezo-electric actuation have been found to be viable options. Power efficiency can be traded away to enable actuation since power is available from the base unit.

FIG. 9 is a perspective view of a probe tip 106 designed according to an embodiment. The scanner 128 with actuator (not shown) and optical components (including focus lens 702) are packaged into a capsule 2.5 mm in diameter and 10 mm in length. This capsule has the meniscus lens 708 as a window at one end, and the electrical leads and single mode fiber 122 exiting at the other end. This capsule design can be incorporated into a number of instruments, thus leveraging development expenses. One form is a 6 mm diameter flexible endoscope. Within this diameter, there is provision for a working channel of typically 2 mm, and an irrigation nozzle for washing particles that might adhere to the window during a procedure. The illustration of FIG. 9 shows eight multimode collection fibers 136 of diameter 1.25 mm. These fibers are sufficiently flexible and can meet bend radius requirements for flexible endoscopy. Alternatively, the few large fibers may be replaced by a collection of many smaller fibers. A greater number of smaller fibers may yield a better fill factor and take better advantage of space available.

The acceptance angle of the collection fibers is matched to the field covered by the scanned light. Because this part of the optical system is non imaging, there is much flexibility in design. The overall determinant is the etendu of the collector, which is the product of the area and collection solid angle. The collected light is then conveyed via multimode fibers and delivered to the etendu of the detector.

The preceding overview of the invention, brief description of the drawings, and detailed description describe exemplary embodiments of the present invention in a manner intended to foster ease of understanding by the reader. Other structures, methods, and equivalents may be within the scope of the invention. As such, the scope of the invention described herein shall be limited only by the claims.

What is claimed is:

1. A scanned beam imaging tip, comprising:
    a single mode optical fiber operative to transmit light to a distal end;
    a focusing lens aligned to receive light from the distal end of the single mode optical fiber;
    a meniscus lens having a semi-reflective inner surface aligned to receive light from the focusing lens and reflect at least a portion of the received light; and
    a MEMS scanner aligned to receive light reflected by the inner surface of the meniscus lens and reflect the light toward a field-of-view and operable to scan the light over a two dimensional field-of-view; and wherein the meniscus lens is operative to shape the light scanned by the MEMS scanner into a beam having a desired shape.

2. The scanned beam imaging tip of claim 1 further comprising at least one multi-mode optical fiber aligned to collect light scattered by the field-of-view and operative to transmit the collected light from a distal to a proximal end.

3. The scanned beam imaging tip of claim 1 wherein the focusing lens is operable to provide a fixed focus.

4. The scanned beam imaging tip of claim 1 wherein the focusing lens is operable to provide a plurality of focal settings.

5. The scanned beam imaging tip of claim 1 wherein the focusing lens is operable to provide continuously-variable focal settings.

6. The scanned beam imaging tip of claim 1 wherein the MEMS scanner includes an aperture aligned to pass light from the focusing lens to the meniscus lens.

7. The scanned beam imaging tip of claim 1 wherein:
    the MEMS scanner includes an aperture aligned to pass light from the focusing lens to the meniscus lens; and
    the focusing lens and semi-reflective inner surface of the meniscus lens are configured to cooperate to produce an illuminated area on the MEMS scanner subtending a greater area than the aperture.

8. The scanned beam imaging tip of claim 1 wherein the light includes a plurality of wavelengths.

9. The scanned beam imaging tip of claim 1 wherein the MEMS scanner is operable to scan the light over a two dimensional field-of-view in a bi-sinusoidal pattern.

10. The scanned beam imaging tip of claim 1 wherein the MEMS scanner is operable to scan the light over a two dimensional field-of-view in a progressively-scanned pattern.

11. A method for imaging a field-of-view comprising:
    transmitting light through a single mode optical fiber to a distal end;
    focusing the light from the distal end of the single mode optical fiber with a focusing lens aligned to receive the light;
    partially reflecting the light from the focusing lens with a meniscus lens having a semi-reflective inner surface aligned to receive light from the focusing lens;
    receiving the light reflected by the inner surface of the meniscus lens with a MEMS scanner and reflecting and scanning the light over a two dimensional field-of-view through the meniscus lens; and
    shaping the scanned light with the meniscus lens into a beam having a desired shape.

12. The method for imaging a field-of-view of claim 11 further comprising:
    collecting light scattered by the field-of-view with at least one multi-mode optical fiber; and
    transmitting the collected light from a distal to a proximal end.

13. The method for imaging a field-of-view of claim 11 wherein the focusing lens is operable to provide a fixed focus.

14. The method for imaging a field-of-view of claim 11 wherein the focusing lens is operable to provide a plurality of focal settings.

15. The method for imaging a field-of-view of claim 11 wherein the focusing lens is operable to provide continuously-variable focal settings.

16. The method for imaging a field-of-view of claim 11 wherein the MEMS scanner includes an aperture aligned to pass light from the focusing lens to the meniscus lens.

17. The method for imaging a field-of-view of claim 11 wherein:

the MEMS scanner includes an aperture aligned to pass light from the focusing lens to the meniscus lens; and the focusing lens and semi-reflective inner surface of the meniscus lens cooperate to produce an illuminated area on the MEMS scanner subtending a greater area than the aperture.

18. The method for imaging a field-of-view of claim 11 wherein the light includes a plurality of wavelengths.

19. The method for imaging a field-of-view of claim 11 wherein the MEMS scanner scans the light over a two dimensional field-of-view in a bi-sinusoidal pattern.

20. The method for imaging a field-of-view of claim 11 wherein the MEMS scanner is scans the light over a two dimensional field-of-view in a progressively-scanned pattern.

* * * * *